(12) United States Patent
Clark et al.

(10) Patent No.: US 7,102,740 B2
(45) Date of Patent: Sep. 5, 2006

(54) METHOD AND SYSTEM FOR DETERMINING SURFACE FEATURE CHARACTERISTICS USING SLIT DETECTORS

(75) Inventors: Bryan Clark, Mountain View, CA (US); Andrei Brunfeld, Cupertino, CA (US)

(73) Assignee: Xyratex Technology Ltd., Hampshire (GB)

( * ) Notice: Subject to any disclaimer, the term of this patent is extended or adjusted under 35 U.S.C. 154(b) by 263 days.

(21) Appl. No.: 10/654,242

(22) Filed: Sep. 3, 2003

(65) Prior Publication Data

US 2005/0046829 A1 Mar. 3, 2005

(51) Int. Cl.
*G01N 21/00* (2006.01)

(52) U.S. Cl. .............................. 356/237.1; 356/237.2; 356/237.5

(58) Field of Classification Search ................ None
See application file for complete search history.

(56) References Cited

U.S. PATENT DOCUMENTS

| | | | | |
|---|---|---|---|---|
| 4,136,949 A | * | 1/1979 | Hayamizu et al. | ......... 356/3.02 |
| 5,424,538 A | * | 6/1995 | Yoshino | ...................... 250/235 |
| 5,444,537 A | * | 8/1995 | Yoshimura et al. | ......... 356/603 |
| 5,606,174 A | * | 2/1997 | Yoshimura et al. | .... 250/559.22 |
| 6,428,171 B1 | * | 8/2002 | Aoki et al. | ................. 356/634 |
| 2003/0067600 A1 | * | 4/2003 | Curtiss | ....................... 356/328 |

* cited by examiner

*Primary Examiner*—Michael P. Stafira
(74) *Attorney, Agent, or Firm*—A. Mitchell Harris; Jeffrey D. Moy; Weiss & Moy P.C.

(57) ABSTRACT

A method and system for determining surface feature characteristics (including position and dimensions) using slit detectors provides a low-cost and high-speed measurement system for inspecting a surface. The system includes multiple slit detectors positioned so that a feature on a surface scanned by the system is detected by at least two detectors that are rotationally offset from each other and from the direction of scanning, a scanning control system for providing motion to the surface of interest in relation to the detectors, and an electronic analyzer for computing characteristics (including position and dimensions) of surface features. The location of surface features along an axis perpendicular to the direction of motion of the surface is determined from the relative timing between the presence of surface feature within the slit detector fields and the dimension of surface features in a direction crossing the short axis of a slit detector field is determined from the relative length of time the features remain in the slit detector field.

19 Claims, 5 Drawing Sheets

METHOD AND SYSTEM FOR DETERMINING SURFACE FEATURE CHARACTERISTICS USING SLIT DETECTORS

CROSS REFERENCE TO RELATED APPLICATIONS

This patent application is related to pending U.S. patent application entitled METHOD AND SYSTEM FOR DETERMINING DIMENSIONS OF OPTICALLY RECOGNIZABLE FEATURES, Ser. No. 10/212,832, which was filed on Aug. 5, 2002 by the same inventor and assigned to the same assignee.

BACKGROUND OF THE INVENTION

1. Field of the Invention

The present invention relates to optical inspection and measuring systems, and more specifically, to an optical method and system for determining characteristics of optically recognizable surface features.

2. Description of the Related Art

Surface inspection systems are in widespread use in industries such as semiconductor and optical device manufacturing for verifying structures in design phases as well as during manufacturing quality inspection. Traditional surface inspection techniques rely on imaging a surface with multiple-pixel imaging systems and processing the resultant signals in order to detect features on the surface. A common surface inspection method uses a camera to capture an image of the entire surface of interest and processing the resultant two-dimensional image to identify surface features. The camera-based technique requires expensive equipment and complex image processing software or hardware. Further, the resolution of the system is limited by camera pixel count and size.

An alternative common method is surface scanning using a line array. The line array technique is generally less complex and expensive than imaging an entire surface. The resolution of a line array may be increased by increasing the pixel count or by joining multiple arrays. However, the scanning speed of the line array technique is limited by the access time required to address and read an intensity value from each pixel.

Inspection systems using a single detector element (point detector) have also been implemented, but while the cost of such elements is low and the access time of the detector is generally much higher than for a line array or camera, the time required for scanning and detecting resultant reflections from every unique point in two dimensions on a surface of interest limits the scanning speed of the point detector.

Therefore, it would be desirable to provide a low cost and high speed surface inspection system that does not require a camera or line array and that does not require a unique scan of every point on a surface of interest in order to detect surface features of the surface of interest.

SUMMARY OF THE INVENTION

The above-stated objectives of low cost and high speed inspection are achieved in a method and optical inspection system that do not required a unique scan of every point on a surface of interest in order to determine characteristics (including position and dimensions) of optically recognizable features. The system includes multiple slit detectors positioned so that a feature on a surface scanned by the system is detected by at least two detectors that are rotationally offset from each other and from the direction of scanning, a scanning control system for providing motion to the surface of interest in relation to the detectors, and an electronic analyzer for computing the characteristics of surface features in conformity with the position and alignment of the detectors and the timing of detection signals as the features traverse the individual fields of detection of the detectors.

The foregoing and other objects, features, and advantages of the invention will be apparent from the following, more particular, description of the preferred embodiments of the invention, as illustrated in the accompanying drawings.

DESCRIPTION OF EMBODIMENTS OF THE INVENTION

Figure 1:
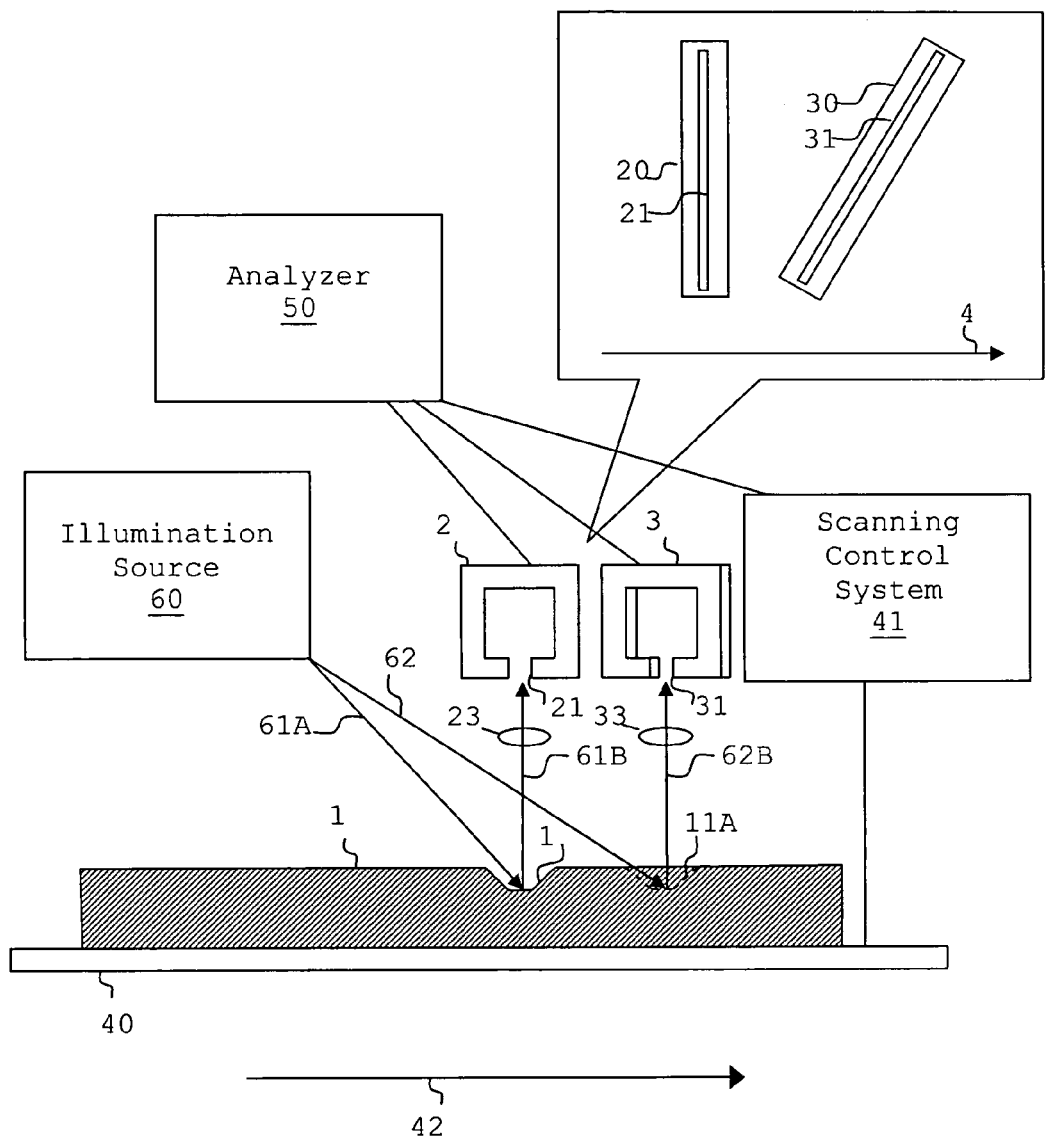
FIG. 1 is an illustration depicting a cross-sectional view of a surface of interest under inspection by a system in accordance with an embodiment of the present invention.

With reference now to the figures, and in particular to FIG. 1, a surface 10 of interest as inspected by a system in accordance with an embodiment of the present invention is depicted. While the illustration depicts a cavity in the surface of interest, in practice any optically recognizable feature of any geometry may be detected by the system of the present invention, such as a protrusion, change in reflectivity, or change in reflective index, et cetera. The system of the present invention provides a mechanism for detecting characteristics of surface features on a surface of interest, including position of the surface feature and dimensions of the surface feature on the surface of interest.

A scanning platform 40, which may be a simple motional positioner, supports surface 10 and moves surface 10 through the optical field of slit detector 20 and the optical field of slit detector 30 along a motional path 42. Detector 20 has a field of detection defined by a projection of a slit field of view 21 upon surface 10. Detector 20 detects light 61B returning on an optical path after being scattered by a feature 11 within field of detection 22. Detector 30 has a field of detection defined by a projection of another slit field of view 31 upon surface 10 by placement in the immediate vicinity of surface or by an imaging lens (23, 33) or lens system included within the detector assembly or otherwise positioned in the optical path as illustrated in the figure. Lenses 23 and 33 are not required if slit detectors 20 and 30 are in close proximity to the surface. The detection field is therefore defined by the slit width and optical magnification between detector 30 and the surface. Detector 30 detects light 62B returning on another optical path after being scattered by feature 11 that has been translated to position 11A within field of detection 32, due to motion of scanning platform 40 with respect to detectors 20 and 30.

Illumination is provided by an illumination source 60 that illuminates surface 10. Illumination source 60 may be any suitable illuminating source, as no coherence or focusing requirement is implicit in the system of the present invention. Detectors 20 and 30 detect variations of received light due to scattering by a surface feature 11. The invention can therefore operate by means of dark field or bright field detection. The invention can also operate using ambient light to illuminate surface 10 instead of separate illumination source 60. Slit detectors as used in the present invention may be implemented with single long PIN photodiodes, optical fiber bundles with standard detectors such as a photodiode at the terminal ends, large area detectors having a slit field of view, or other devices that produce the slit fields used to detect surface feature characteristics as described herein.

The present invention separates detection of the position of feature 11 in the time domain by moving surface 10 relative to detectors 20 and 30, as controlled by a scanning control system 41. Surface 10 may move while detectors 20 and 30 remain stationary, or detectors 20 and 30 may move while surface 10 remains stationary. Alternatively, instead of moving surface 10 or detectors 20 and 30, the surface image may be scanned (moved) relative to the detectors using one of many known image scanning techniques, such as a plane mirror resonant scanner, a polygonal rotating mirror, or a multi-mirror sideways scanner such as a corner-cube arrangement. Also, scanning control system 41 may move surface 10 at a constant velocity relative to detectors 20 and 30, eliminating a need to synchronize control system 41 with analyzer 50.

Figure 2:
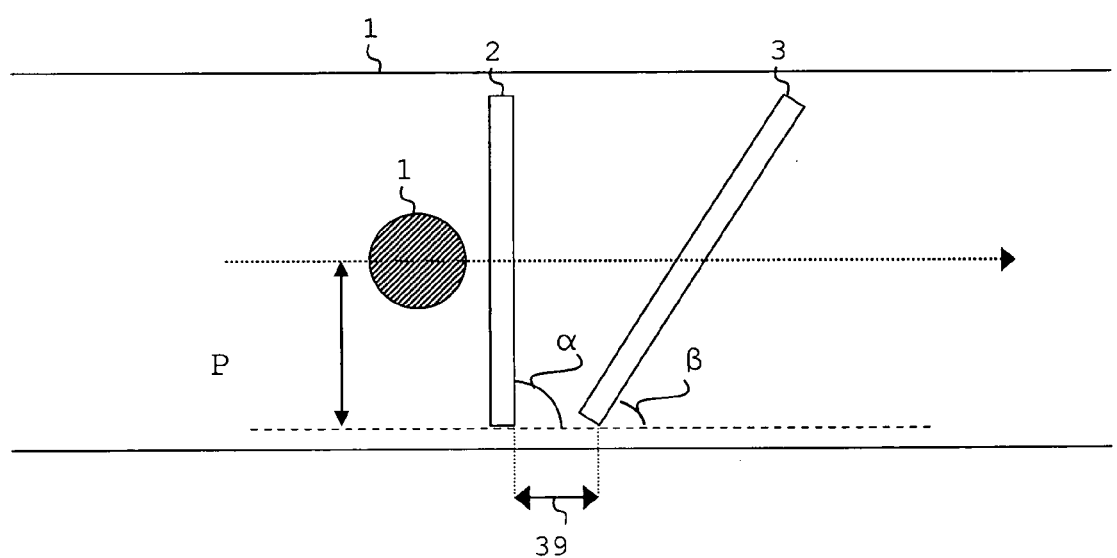
FIG. 2 is an illustration depicting an overhead view of the surface of interest and system of FIG. 1.

FIG. 2 depicts an overhead view of an embodiment of the present invention positioned over a surface of interest with an optically recognizable surface feature. As a scanning system moves surface of interest 10 in direction 42, feature 11 passes through fields of detection 22 and 32. Fields of detection 22 and 32 as projected onto surface 10 are substantially rectangular, each having a long axis and a short axis and are aligned with long axes positioned at differing predetermined angles $\alpha$ and $\beta$ to motional path 42.

Figure 3:
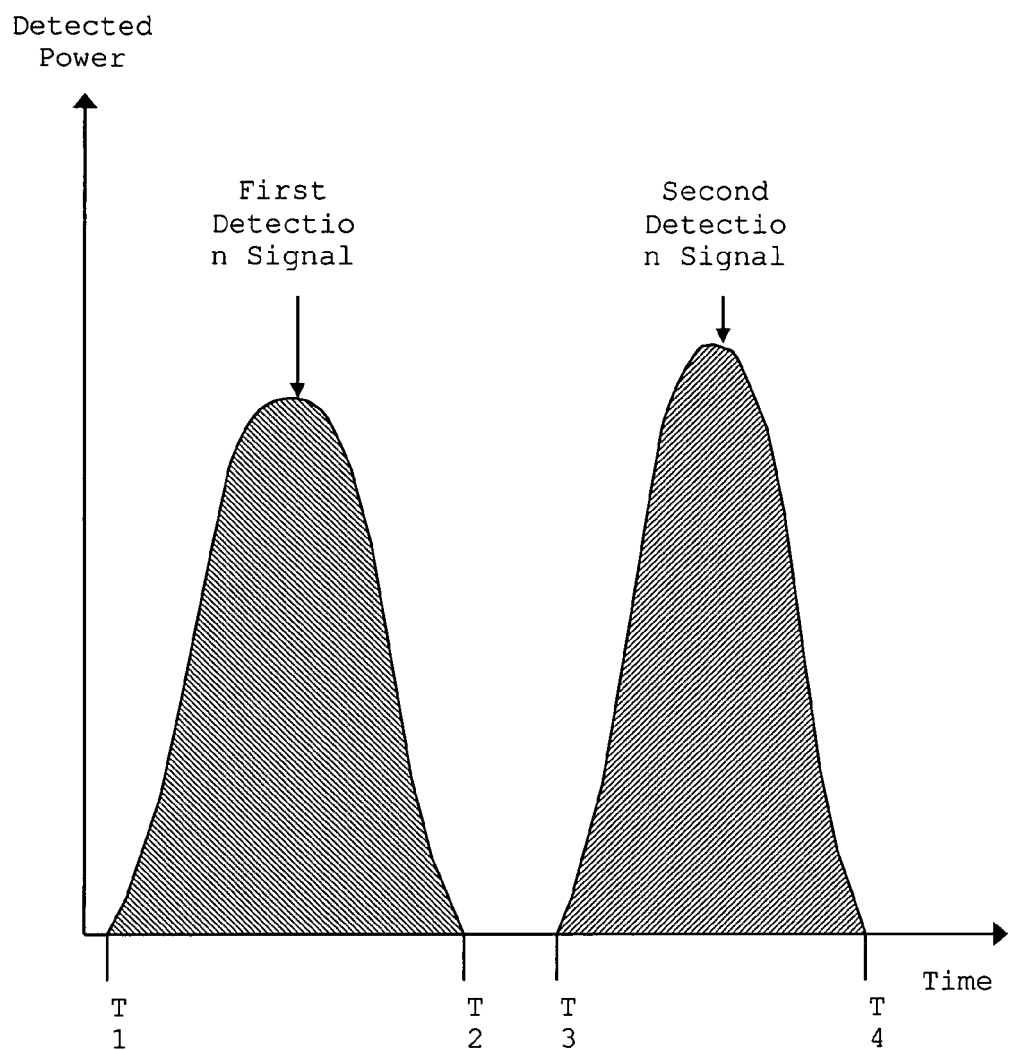
FIG. 3 is a timing diagram depicting outputs of detectors 20 and 30 of FIG. 1 as a surface feature is moved through the fields of detectors 20 and 30 over time.

FIG. 3 depicts the time response of detectors 20 and 30 to received light scattered by feature 11. Prior to time T1, no feature is detected and the output signal of both detectors is an ambient signal, defined in FIG. 3 as zero reference level signal. At time T1, the feature enters field of detection 22 of first detector 20, causing first detector 20 to generate a non-zero output signal. As feature 11 crosses field of detection 22 of first detector 20, the increasing area of feature 11 within field of detection 22 of first detector 20 causes an increase in the first detection output signal which reaches a peak at the midpoint of feature 11. The output signal of detector 20 then decreases to zero until feature 11 leaves field of detection 22 at time T2. No output signal is generated by detectors 20 or 30 until time T3, when feature 11 enters field of detection 32 of second detector 30. As feature 11 crosses field of detection 32 of second detector 30, the output signal of second detector 30 increases to a peak at the midpoint of feature 11 and then decreases to zero as feature 11 leaves field of detection 32 at time T4.

An offset 39 between fields of detection 22 and 32 in the direction of motion 42 may be employed to introduce additional distinction between the output signals of detector 20 and 30 for real-time surface inspection. In addition, imaging systems may be employed to modify the configuration or characteristics of fields of detection 22 and 32 on the surface of interest.

Due to the angular offset between fields of detection 22 and 32, the distance between fields of detection 22 and 32 varies linearly with position. As a result, a measured time difference between a feature's first detection and second detection locates the position of that feature perpendicular to the direction of motion 42 in accordance with a known surface scan speed or in accordance with a mapping of detected positions of a positioner. The position P of a surface feature perpendicular to the direction of motion is computed as:

$$P = \frac{x_0 - x_t}{\cotan \alpha - \cotan \beta}$$

where $x_0$ is offset 39 and $x_t = v \cdot (T3-T1)$, where v is a constant scanning speed, T1 is the time of detection by detector 20, and T3 is the time of detection by detector 30. Although times T1 and T3, and therefore P, vary with feature geometry, $\alpha$ and $\beta$, this effect becomes negligible as the dimensions of the system far exceed the dimensions of the feature. Further, interpolation can be employed to further increase the resolution of the system.

The angular offset of fields of detection 22 and 32 also provides determination of a dimension of feature 11 along the short axis of each field 22 and 32. For example, the dimension D20 of a feature along the short axis of detector 20 is determined by:

$$D20 = \frac{v(T2 - T1)}{\sin \alpha}$$

where T2−T1 is the duration of detection by detector 20, v is a constant scanning speed.

In addition, because the output signal of detector 20 or 30 in response to a feature in the detector's field of detection 22 or 32 is proportional to the area of field of detection 22 or 32 occupied by the feature, the area A of a maximum cross-section of a feature within a field of detection 22 or 32 may be computed in accordance with the accumulated magnitude of the detection signal during the period of detection. For example, the area of feature 11 passing through field of detection 22 is given by:

$$A = K \int_{T1}^{T2} s_{20}(t) dt$$

where K is a constant of proportionality and $s_{20}(t)$ is the output signal of detector 20 as a function of time. For discrete signal sampling a discrete expression for the above integral equation is:

$$A = \frac{K}{f} \sum_{T=T1}^{T2} S_{20}(T)$$

where K is a constant of proportionality and $S_{20}(T)$ is the output signal of detector 20 at time T, and f is the sampling frequency.

An electronic analyzer 50 includes a processor (including the necessary circuitry to capture and convert the output of detectors 20 and 30 to digital form and perform interpolation if required), coupled to detectors 20 and 30 and scanning control system 41. The processor includes a memory for storing program instructions for execution by an instruction unit and data values for manipulation by the program instructions. Program instructions for implementing portions of the method of the present invention include program instructions for receiving the output signal from detectors 20 and 30, detecting surface features and computing positions of detected features in a direction perpendicular to direction of motion 42 in conformity with the time difference between the detection of the feature by detector 20 and detector 30. The program instructions also include program instructions for computing the dimension of detected surface features along a short axis of field of detection 22 or 32 of detector 20 or 30 on surface 10 in conformity with the time of detection by that detector, and computing the area of the intersection of a surface feature with surface of interest 10 in conformity with an accumulated magnitude of the detection signal by detector 20 or 30.

Figure 4:
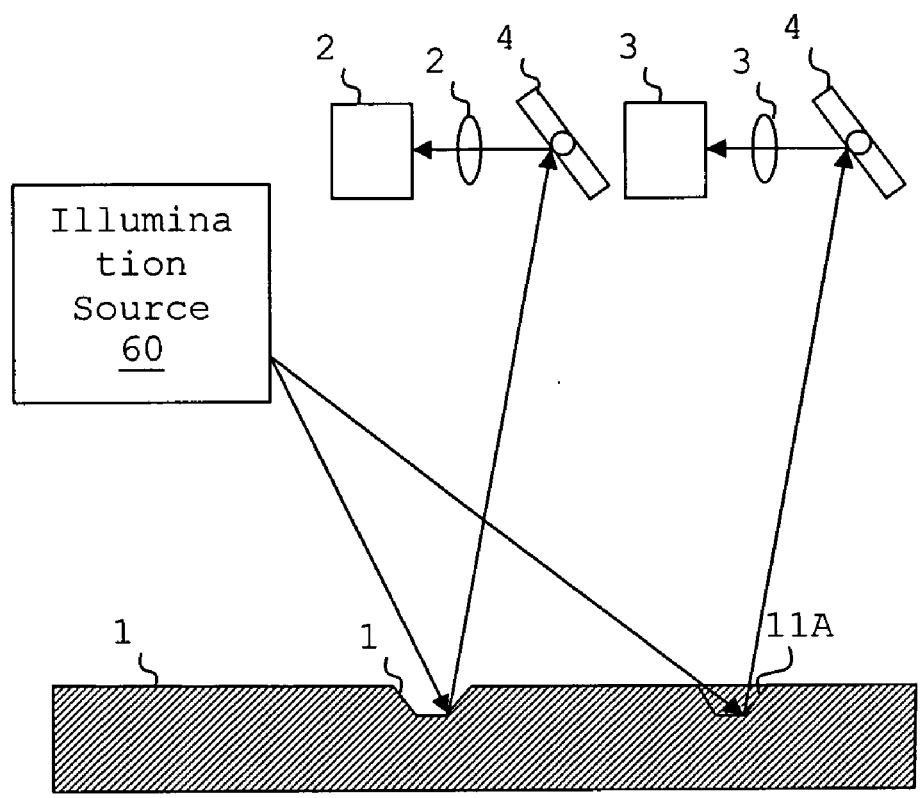
FIG. 4 is an illustration depicting a cross-sectional view of a surface of interest under inspection by a system in accordance with an embodiment of the present invention with an optical scanning system and imaging elements.

FIG. 4 depicts a cross sectional view of surface of interest 10 under inspection by an alternative embodiment of the present invention. In this embodiment, optics 23 and 33 image light from field of detection 22 onto detector 20 and from field of detection 32 onto detector 30. An optical scanning system comprising synchronously aligned reflective elements 42 and 43 translates fields of detection 22 and 32 along surface 10 to detectors 20 and 30.

Figure 5:
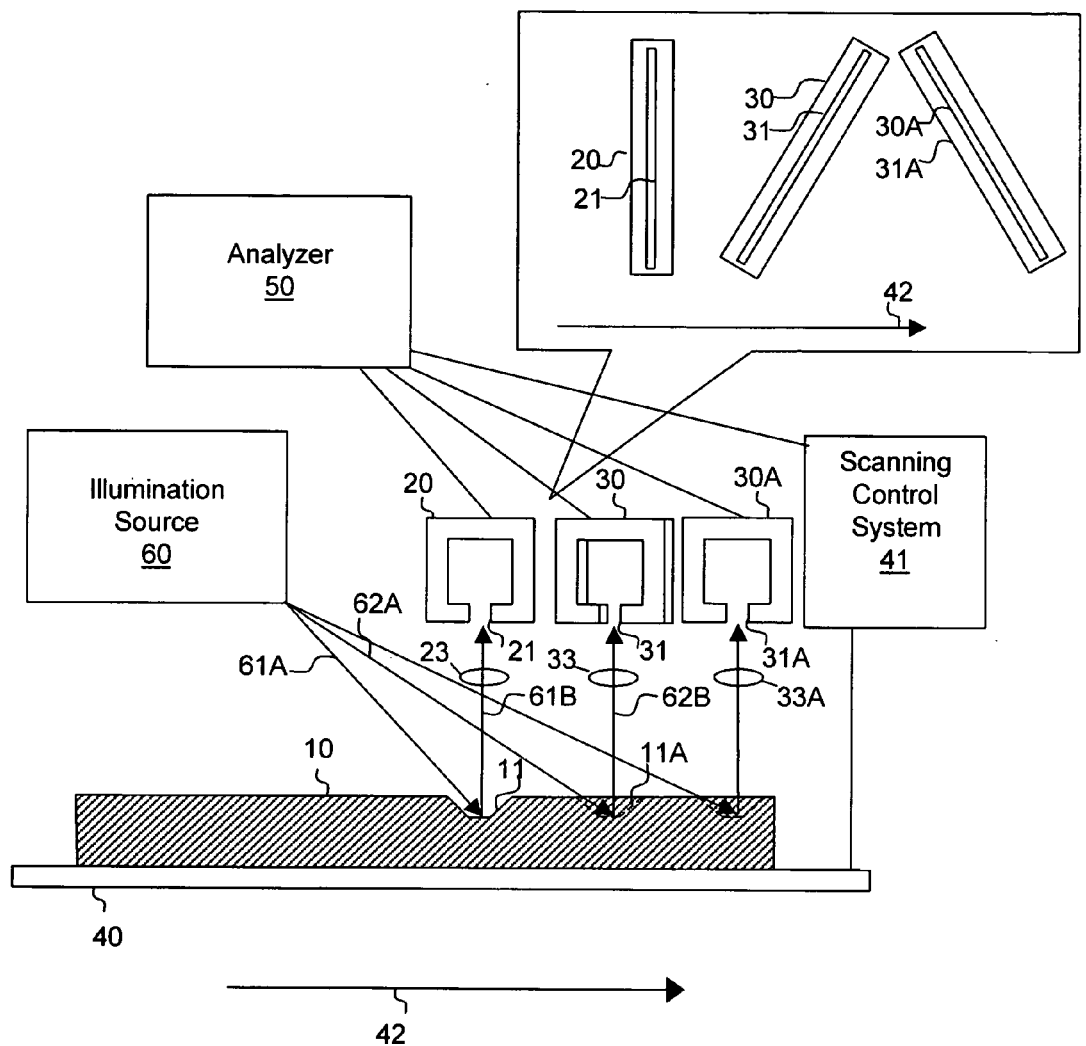
FIG. 5 is an illustration depicting a cross-sectional view of a surface of interest under inspection by a system in accordance with another embodiment of the present invention.

Only two detectors are required to implement the techniques of the present invention, but the invention is not limited to two detectors. Additional detectors, such as detector 30A of FIG. 5, which provides another slit field of view 31A and may include optics 33A as used with other detectors 20 and 30, may be used to further improve spatial resolution for surfaces where a high feature density may generate ambiguous signals due to multiple features within the detector fields. Since the speed of translation is effectively constant, use of multiple detectors provides for resolution of multiple ambiguities. Further, additional detectors may be used to increase scanning width without proportionally reducing the detection signal of a surface feature in the larger detectors.

The 2-D scanning method of the present invention provides higher resolution than available from traditional multi-pixel techniques that are limited by pixel size. In the method and system of the present invention, the resolution is transferred from the spatial to the temporal domain and is instead limited by detector response and timing accuracy. Resolution can therefore be several times higher than that of multi-pixel systems. Moreover, the method of the present invention eliminates the delay inherent in multi-pixel systems resulting from signal framing and transferring pixel data from an array to processing elements.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system comprising:
a first slit detector having a first slit field of view, wherein said first slit field of view has a first longitudinal axis aligned at a first predetermined angle of projection along a direction of optical translation of said detector with respect to a surface of interest for detecting light traveling in a first optical path extending from said surface of interest to said first detector;

a second slit detector having a second slit field of view, wherein said second slit field of view has a second longitudinal axis aligned at a second predetermined angle of projection along said direction of said optical translation for detecting light traveling in a second optical path extending from said surface of interest to said second detector, and wherein said second predetermined angle differs from said first predetermined angle;

a scanning system for generating said optical translation of said surface of interest with respect to both of said first and second detectors; and an electronic analyzing system coupled to said first and second detectors and said scanning system for detecting a characteristic of a surface feature on said surface of interest, in conformity with a time difference of output signals from at least one of said first slit detector and said second slit detector.

2. The optical system of claim 1, wherein said second slit axis of said second detector is offset a predetermined distance in said direction of optical translation from said first slit axis of said first detector.

3. The optical system of claim 1, wherein said electronic analyzing system comprises a processor for computing a position of said surface feature in a plane of said surface of interest and in a direction perpendicular to said direction of optical translation in conformity with the time difference between detection of said surface feature by said first detector and detection of said surface feature by said second detector.

4. The optical system of claim 1, wherein said electronic analyzing system comprises a processor for computing a first projected length of said surface feature in a direction perpendicular to said first longitudinal axis of said first detector in conformity with a first time interval during which said surface feature transverses a first field of said first slit field of view.

5. The optical system of claim 4, wherein said processor further computes a second projected length of said surface feature in a direction perpendicular to the slit axis of said second detector in conformity with a second time interval during which said surface feature transverses a second field of said second slit field of view.

6. The optical system of claim 5, wherein said processor computes a cross-sectional area of said surface feature in the plane of said surface of interest in conformity with a first accumulated magnitude of a variation of light scattered by said surface feature and detected by said first detector as said surface feature traverses said first field of said first slit field of view and a second accumulated magnitude of a variation of light scattered by said surface feature and detected by said second detector as said surface feature traverses said second field of second slit field of view.

7. The optical system of claim 1, further comprising a first imaging system positioned in said first optical path and a second imaging system positioned in said second optical path, whereby light scattered from said surface feature is imaged on said first and second detectors.

8. The optical system of claim 1, wherein said scanning system is a scanning table for translating said surface of interest with respect to said first detector and said second detector.

9. The optical system of claim 1, wherein said scanning system is a head scanning system for translating said first detector and said second detector with respect to said surface of interest.

10. The optical system of claim 1, wherein said scanning system is an optical scanning system positioned in said first optical path and said second optical path for translating said first optical path and said second optical path across said surface of interest in said direction of optical translation.

11. The optical system of claim 1, further comprising a third detector coupled to said electronic analyzing system and having a third slit field of view, wherein said third slit field of view has a third longitudinal axis aligned at a third predetermined angle of projection along said direction of said optical translation for detecting light traveling in a third optical path extending from said surface of interest to said third detector, and wherein said third predetermined angle differs from said first and second predetermined angles, whereby said third detector provides input to said electronic analyzing system for resolving ambiguities.

12. A method for determining position and dimensions of a surface feature on a surface of interest, comprising:
optically translating said surface of interest;
first detecting light scattered from said surface feature to a first slit field of view having a first longitudinal axis aligned at a first predetermined angle of projection along a direction of said optically translating;
second detecting light scattered from said surface feature to a second slit field of view having a second longitudinal axis aligned at a second predetermined angle of projection along said direction of said optically translating; and
computing a characteristic of said surface feature in conformity with a result of said first detecting and said second detecting.

13. The method of claim 11, further comprising offsetting a projection of said first slit field of view and a projection of said second slit field of view on said surface of interest by a predetermined distance.

14. The method of claim 12, further comprising:
in response to said first detecting, first storing an indication of a first position of said optically translating;
in response to said second detecting, second storing an indication of a second position of said optically translating; and
computing said position of said surface feature in said direction perpendicular to said direction of said optically translating by calculating a difference between said first indication and said second indication and scaling said difference by a trigonometric function of the angular difference between said first and second predetermined angles.

15. The method of claim 12, further comprising:
in response to said first detecting detecting that said surface feature has entered a first field of said first optical aperture, first storing an indication of a first position of said optical translation;
in response to said first detecting detecting that said surface feature has exited said first field, second storing a second position of said optical translation, and wherein said computing computes a first projected length of said surface feature in a direction of said first predetermined angle in conformity with a first difference between said first indication and said second indication.

16. The method of claim 15, further comprising:
in response to said second detecting detecting that said surface feature has entered a second field of said second optical aperture, third storing a third indication of a third position of said optical translation;
in response to said second detecting detecting that said surface feature has exited said second field, fourth storing a fourth indication of a fourth position of said optical translation; and
computing a second projected length of said surface feature in a direction of said second predetermined angle in conformity with a second difference between said third position and said fourth position.

17. The method of claim 12, wherein said optically translating translates said surface of interest while said first slit field of view and said second slit field of view remain fixed.

18. The method of claim 12, wherein said optically translating translates said first slit field of view and said second slit field of view while said surface of interest remains fixed.

19. The method of claim 11, further comprising:
first imaging light scattered from said surface feature into said first slit field of view; and
second imaging light scattered from said surface feature into said second slit field of view.

* * * * *